United States Patent [19]

Arcamone et al.

[11] 4,098,798
[45] Jul. 4, 1978

[54] ADRIAMYCINS, PROCESS FOR THEIR PREPARATION AND USES THEREOF

[75] Inventors: Federico Arcamone; Aurelio Di Marco; Sergio Penco, all of Milan, Italy

[73] Assignee: Societa' Farmaceutici Italia S.p.A., Milan, Italy

[21] Appl. No.: 823,581

[22] Filed: Aug. 11, 1977

Related U.S. Application Data

[62] Division of Ser. No. 560,104, Mar. 19, 1975, Pat. No. 4,058,519.

[30] Foreign Application Priority Data

Mar. 22, 1974 [GB] United Kingdom ............... 12783/74

[51] Int. Cl.$^2$ ............................................. C07D 317/10
[52] U.S. Cl. ............................................. 260/340.9 R
[58] Field of Search .................................. 260/340.9 R

[56] References Cited

U.S. PATENT DOCUMENTS 3,651,090  3/1972  Hardie et al. ...................... 260/340.9

Primary Examiner—Ethel G. Love
Attorney, Agent, or Firm—Hubbell, Cohen, Stiefel & Gross

[57] ABSTRACT

The known antibiotics adriamycin and its β-anomer, and the novel compounds, 4'-epiadriamycin (both α- and β-anomers) are prepared by condensing a novel, reactive protected derivative of adriamycinone with reactive intermediates which are 1-halo-2,3,6-trideoxy-3-trifluoroacetamido-4-trifluoroacetoxy-α-L-lyxo (or arabino) hexopyranoses.

2 Claims, 1 Drawing Figure

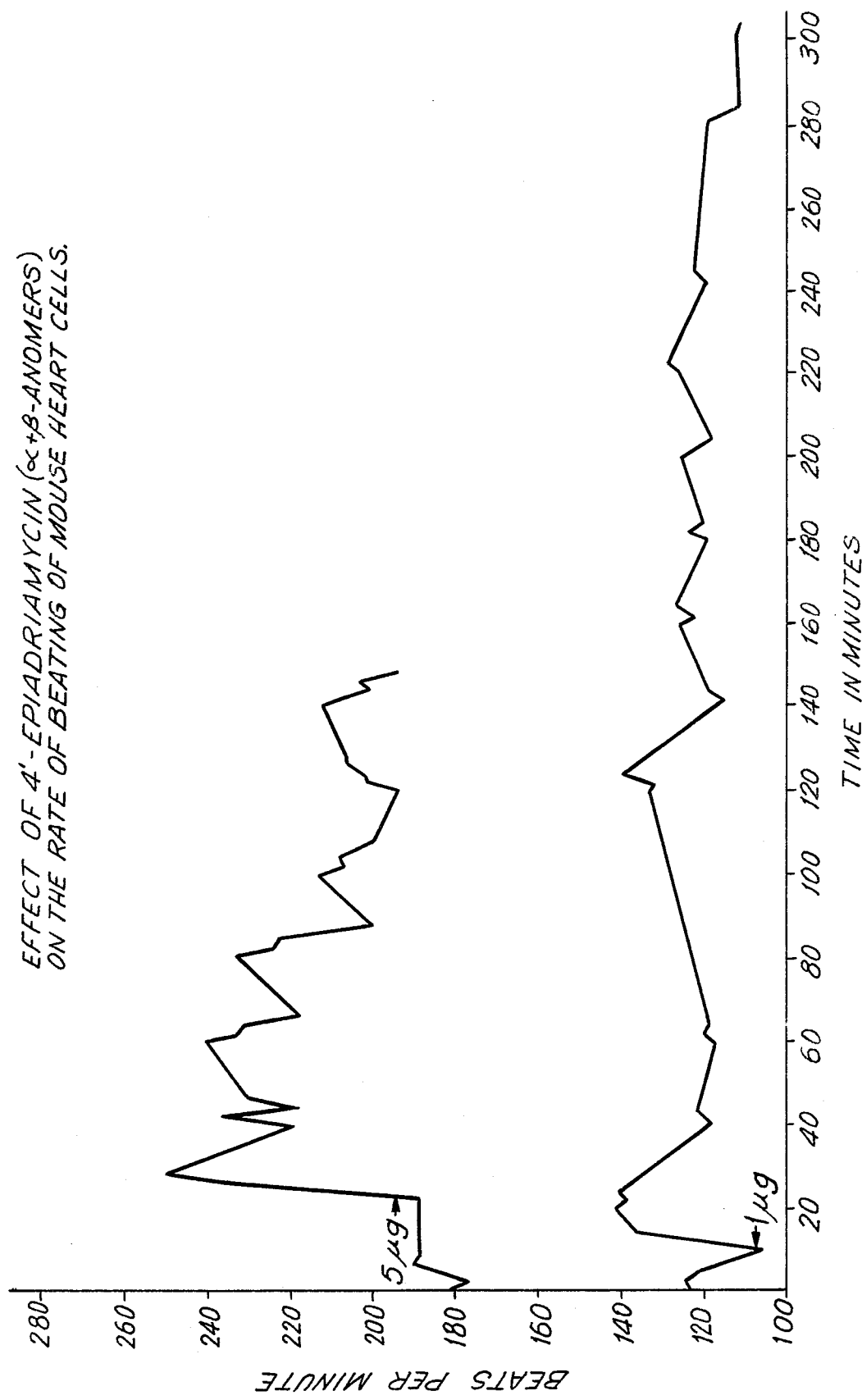

ADRIAMYCINS, PROCESS FOR THEIR PREPARATION AND USES THEREOF

CROSS REFERENCE TO RELATED APPLICATIONS:

This is a division of application Ser. No. 560,104, filed Mar. 19, 1975, now U.S. Pat. No. 4,058,519.

BACKGROUND OF THE INVENTION

1. Field of the Invention

The present invention relates to a new process for the synthesis of the known antibiotics adriamycin and its β-anomer. The invention also relates to the new compounds: 4'-epiardriamycin α-anomer, 4'-epiadriamycin β-anomer and a mixture thereof as well as a process for preparing same. The new processes for preparing adriamycin and 4'-epiadriamycin involves the preparation and use of a new, reactive, protected intermediate derivative of adriamycinone, the aglycone of adriamycin which new derivative is also included within the invention. The new compounds of the invention, i.e., 4'-epiadriamycin (α- and β-anomers) as well as the known adriamycin are useful in treating certain tumors in animals.

2. Description of the Prior Art

Adriamycin and its aglycone adriamycinone are well known compounds. They are, for example, described and claimed in British Pat. Nos. 1,161,278 and 1,217,133 owned by the unrecorded assignee of this application.

SUMMARY OF THE INVENTION

The present invention provides, in one aspect thereof, a new process for preparing adriamycinone glycosides. More specifically, the invention provides a process, which in one embodiment is used for preparing the known compound adriamycin (IV), i.e., 7-O-(3'-amino-2',3',6'-trideoxy-α-L-lyxohexopyranosyl)-adriamycinone,

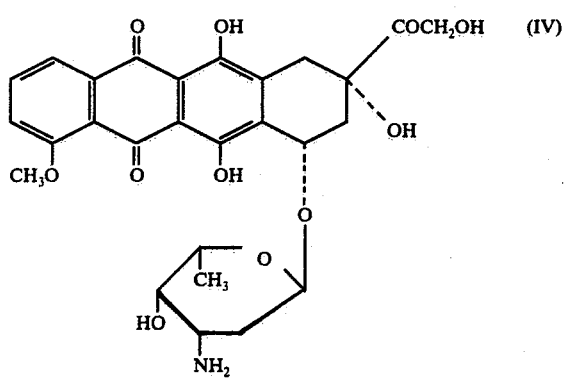

and its β-anomer (V), i.e., 7-O-(3'-amino-2',3',6'-trideoxy-β-L-lyxohexopyranosyl)-adriamycinone, by condensing a novel dioxolanyl protected derivative of adriamycinone (IB)

wherein $R_1$, $R_2$ and $R_3$ are independently selected from the group consisting of hydrogen and $C_1$–$C_4$ alkyl; or $R_2$ and $R_3$ together with the carbon atom to which they are bound may form a saturated or unsaturated ring of 3–8 carbon atoms, preferably, the dioxolanyl derivative wherein each of $R_1$, $R_2$ and $R_3$ is methyl, i.e., the compound having the formula (IC)

with a reactive protected derivative of daunosamine (II), i.e., 3-amino-2,3,6-trideoxy-L-lyxohexose, to form the glycosidic linkage after which the protecting groups, i.e., the trifluoroacetyl groups on the daunosamine and the dioxolanyl protecting group on the adriamycinone moiety of the glycoside are removed and the α- and β-anomers are separated. The novel dioxolanyl protected derivatives of adriamycinone (IB) which are condensed with the daunosamine derivative are prepared by reacting adriamycinone (I)

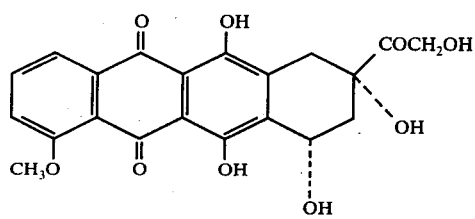

(I), or a $C_1$–$C_4$ alkyl ester thereof with a compound of the formula

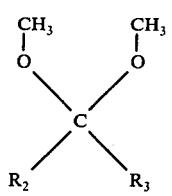

wherein $R_2$ and $R_3$ are independently selected from the group consisting of $C_1$–$C_4$ alkyl or $R_2$ and $R_3$ together with the carbon atom to which they are bound may form a saturated or unsaturated ring of 3–8 carbon atoms, in the presence of an organic or inorganic acid, such as p-toluene-sulfonic acid or hydrogen chloride.

The reactive protected derivative of daunosamine which is condensed with the adriamycinone derivative (IB) is the intermediate 1-chloro-2,3,6-trideoxy-3-trifluoroacetamido-4-trifluoroacetoxy-α-L-lyxohexopyranose (IIB)

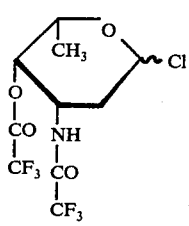

(IIB)

which is in turn obtained from the intermediate, 2,3,6-trideoxy-1-trifluoroacetoxy-3-trifluoroacetamido-4-trifluoroacetoxy-L-lyxohexopyranose (IIA),

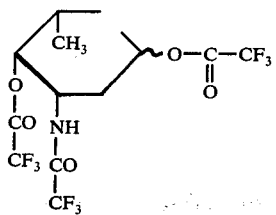

(IIA), compound (IIA) being in turn prepared by reacting daunosamine (II) with trifluoroacetic anhydride.

This same process, in another embodiment is used for preparing the novel antibiotics 4'-epiadriamycin (VI), i.e., 7-0-(3'-amino-2',3',6'-trideoxy-α-L-arabinohexopyranosyl)-adriamycinone

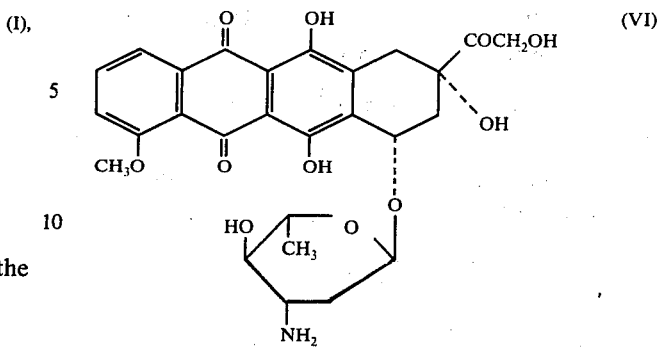

(VI)

and its β-anomer (VII), i.e., 7-0-(3'-amino-2',3',6'-trideoxy-β-L-arabinohexopyranosyl)-adriamycinone

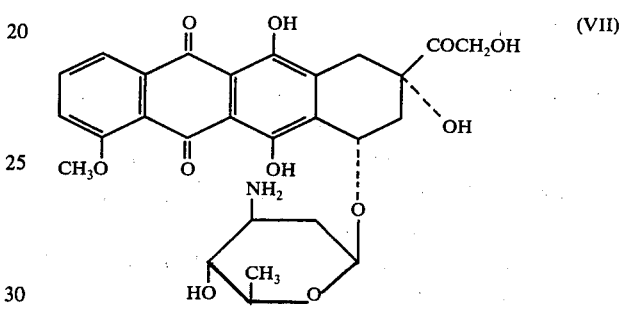

(VII)

as a mixture of the two anomers as well as each anomer separately. To prepare 4'-epiadriamycin (VI) and its β-anomer (VII), the dioxolanyl protected derivative of adriamycinone (IB) is condensed, as described above, with a reactive protected derivative of 4'-epidaunosamine (III), i.e., 3-amino-2,3,6-trideoxy-L-arabinohexose,

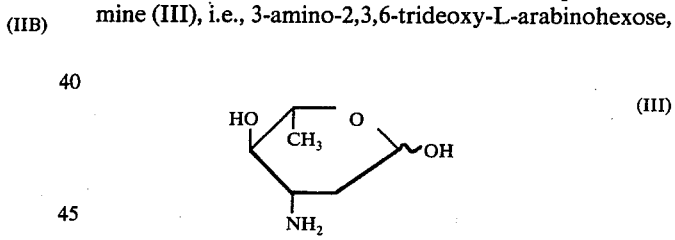

(III)

to form the glycosidic linkage, after which the protecting groups on the adriamycinone moiety and on the 4'-epidaunosamine are removed and the α- and β-anomers are separated. The reactive protected derivative of 4'-epidaunosamine which, in this embodiment is consensed with (IB) is, 1-chloro-2,3,6-trideoxy-3-trifluoroacetamido-4-trifluoroacetoxy-α-L-arabinohexopyranosc (IIIB)

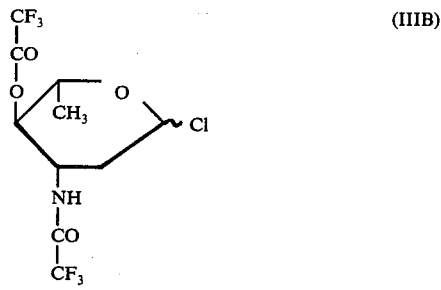

(IIIB)

which is obtained from the intermediate, 2,3,6-trideoxy-1-trifluoroacetoxy-3-trifluoroacetamido-4-trifluoroacetoxy-I-arabinohexopyranose (IIIA)

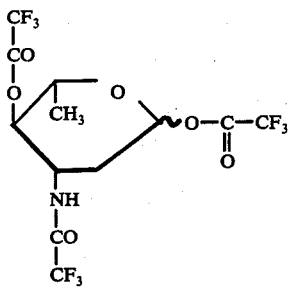

(IIIA)

compound (IIIA) being in turn prepared by reacting 4'-epidaunosamine (III) with trifluoroacetic anhydride. Thus, it is clear that the only essential difference between the two embodiments is the nature of the starting sugar which is reacted (in the form of a reactive protected derivative) with the protected dioxolanyl derivative (IB) of the aglycone (adriamycinone (I)) to form the glycoside. In one embodiment this sugar has the L-lyxose configuration and in the other it has the L-arabinose configuration.

In another aspect, the invention provides the novel antibiotic end products (VI) 4'-epiadramycin (α-anomer) and (VII) 4'-epiadriamycin (β-anomer) as well as the novel intermediates of the formula (IB), which are protected dioxolanyl derivatives of adriamycinone, and which are used in the preparation of adriamycin and the novel 4'-epiadriamycin.

In a further aspect, the invention provides methods of using the novel antibiotic end products (VI) and (VII) in treating various mammalian tumors.

The process of the invention, as stated above, broadly comprises condensing a protected derivative of adriamycinone (I), and in particular, a derivative wherein the primary OH group of the side chain is protected, e.g., a dioxolanyl derivative of the formula (IB), preferably, the compound of the formula (IC), with a derivative of daunosamine (II) or 4'-epidaunosamine (III) to obtain the pharmacologically active glycosides (IV) (adriamycin) and (V) or (VI) and (VII). In practice, the hexose (II) or (III) must first be protected, for example, by forming the tri-trifluoro acetyl derivatives (IIA) and (IIA) and then converted into reactive derivatives, such as the 1-halides and in particular, the 1-chloro derivatives (IIB) and (IIIB) which are suitable for condensation with the adriamycinone derivative (IB), or preferably, (IC). After the condensation reaction, the protecting dioxolanyl group on the adriamycinone moiety, and the protecting trifluoroacetyl groups on the hexose are removed to yield the free glycosides.

The 3-amino groups in the hexoses (II) and (III) must be protected with groups that can subsequently be removed without further decomposition of the products which contain different chemically-sensitive groups. The trifluoroacetyl group meets this criterion since it can be readily removed by mild alkaline treatment.

The hexoses (II) and (III) also have to be converted into reactive derivatives that are endowed with sufficient stability to be used in the condensation reaction with the protected adriamycinone (IB) or (IC). The instability of the 1-halo derivatives of 2-deoxysugars is well documented (W. W. Zorbach et al., Advances in Carbohydrate Chemistry, 1966 21, 273). However, according to the invention, it has been found that if the 3-amino and the 1 and 4 hydroxy groups of the hexoses (II) and (III) are protected with trifluoroacetyl groups, the tri-trifluoroacetyl derivatives (IIA) and (IIIA) of the hexoses (II) and (III) can then be reacted with dry hydrogen chloride to give the corresponding 1-chlorohexoses (IIB) and (IIIB). These latter compounds are solid materials which can be stored for several days under anhydrous conditions.

The tri-trifluoroacetyl derivatives (IIA) and (IIIA) are prepared by reacting, under anhydrous conditions, the hexoses (II) and (III), either as such, or as the hydrochloride, with trifluoroacetic anhydride at about 0° C in an inert solvent such as diethyl ether.

The 1-chloro derivatives (IIB) and (IIIB) are then prepared by reacting the tri-trifluoroacetyl derivatives (IIA) and (IIIA), under anhydrous conditions, with anhydrous gaseous hydrogen chloride, in an inert solvent, such as diethyl ether, at a temperature of about 0° C.

The reactive 1-chloro derivative (IIB) or (IIIB) is then reacted with the protected adriamycinone derivative (IB) or (IC) to form the glycoside linkage, after which the protecting dioxolanyl and trifluoroacetyl groups are removed and the product is separated into the respective α- and β-anomers. Alternatively, the α- and β-anomers can be separated before removal of the protecting trifluoroacetyl groups.

The conditions under which the condensation reaction is effected are modifications of the well known Koenigs-Knorr reaction (Conchie et al., Advances in Carbohydrate Chemistry, 1957, 12, 157). This standard reaction contemplates the use of a wide variety of different reaction conditions such as temperature, solvent, catalyst and hydrogen chloride (or bromide) acceptor. However, ordinarily, an optimal set of conditions is necessary to achieve a significant reaction rate. Since the use of the standard Koenigs-Knorr reaction conditions with the 1-halo derivatives of 2-deoxy sugars leads to the unwanted formation of the corresponding glycals (Zorbach et al., supra), it is necessary, according to the present invention, to modify those conditions.

The procedure according to the invention therefore comprises reacting the protected adriamycinone derivative (IB or IC), prepared as described above, with the 1-chloro-N,O-di-trifluoroacetyl derivative (IIB) or (IIIB) of hexose (II) or (III) in an inert organic solvent such as chloroform or methylene dichloride, under mild conditions, in the presence of a catalyst comprising a mercuric halide, for example, mercuric bromide, a hydrogen chloride acceptor, for example, mercuric oxide, silver carbonate, silver oxide, cadmium carbonate, and a dehydrating agent, for example, molecular sieve.

The reaction products, which is either a mixture of the glycosides (IV) and (V) or (VI) and (VII), wherein the adriamycinone moiety is protected with a dioxolanyl group and the sugar moiety is protected with the fluoroacetyl groups are then treated, in two steps, first with a dilute alkali, such as sodium hydroxide to effect removal of the N-trifluoroacetyl groups and second with a dilute acid, such as hydrochloric acid to effect hydrolysis of the cyclic ketal on the side chain, i.e., the dioxolanyl group, to thereby obtain the final products (IV) and (V) or (VI) and (VII). The respective α- and β-anomers are then separated, for example, by fractional crystallization or chromatographic techniques.

BRIEF DESCRIPTION OF THE DRAWING

The drawing is a graph showing the effect of a mixture of (VI) and (VII) on the rate of beating of mouse heart cells in vitro.

DESCRIPTION OF THE PREFERRED EMBODIMENTS

The following examples are given to illustrate the invention without, however, being a limitation thereof. All parts given are by weight unless otherwise indicated.

EXAMPLE 1

Preparation of 9-desacetyl-9-(2',2'-dimethyl-4'-methoxy-4'-dioxolanyl)-daunomycinone (IC)

One gram of adriamycinone (I) in 10 ml. of dioxane and 200 ml. of chloroform was treated with 80 ml. of dimethoxypropane and 0.17 gm. of p-toluenesulfonic acid. The resulting mixture was left standing for 24 hours at room temperature, after which 0.34 gm. of sodium bicarbonate was added and the mixture stirred for five minutes. The organic layer was repeatedly extracted with water to neutrality, dried over anhydrous sodium sulphate, filtered, and evaporated under reduced pressure. The residue was then placed on the top of a silicic acid column, and elution was effected using a 10:1 (by volume) chloroform:acetone solvent system. The main reaction product, which was identified by analytical thin layer chromatography (Rf = 0.38 using silica gel plates and the above solvent system), is 9-desacetyl-9-(2',2'-dimethyl-4'-methoxy-4'-dioxolanyl)-daunomycinone (IC) in the form of a mixture of epimers. Compound (IC) was characterized by NMR, IR and mass spectra, with the following results having been obtained:

NMR (CDCl$_3$): 1.48 e 1.65 (two s, geminal CH$_3$); 3.47 (s, CH$_3$O—C(13)); 4.0–4.6 (m, C(14)H$_2$); 13.02 e 13.71 (two s, chelated OH at C-6 and C-11).

IR (KBr): carbonyl absorption band at 1725 cm.$^{-1}$ which is typical of adriamycinone was absent.

MS (DIS): 486 m/e (M$^+$); 454 m/e (M—32=M—CH$_3$OH); 450 m/e (M—36=M—2H$_2$O); 438 m/e (M—58=M—CH$_3$COCH$_3$); 131 m/e substituted dioxolanyl.

EXAMPLE 2

Preparation of 1-chloro-2,3,6-trideoxy-3-trifluoroacetamido-4-trifluoroacetoxy-α-L-lyxohexopyranose (IIB)

One gram of daunosamine (II) hydrochloride was suspended in anhydrous diethyl ether and treated at 0° C. with 8 ml. of trifluoroacetic anhydride. After allowing the suspension to stand for two hours at 0° C. and one hour at room temperature, the solvent was removed under reduced pressure and the residue was crystallized from dichloromethane to yield 1.1 g. of 2,3,6-trideoxy-1-trifluoroacetoxy-3-trifluoroacetamido-4-trifluoroacetoxy-L-lyxopyranose (IIA), having a m.p. of 132°–134° C. and a mass spectrum m/e 391 (M-44), 322 (M-113). 0.5 g of (IIA) in anhydrous diethyl ether was treated at 0° C. with anhydrous gaseous hydrogen chloride. After standing at +5° C. overnight, the solvent was removed in vacuo to yield 1-chloro-2,3,6-trideoxy-3-trifluoroacetamido-4-trifluoroacetoxy-α-L-lyxohexopyranose (IIB) as crystalline product. The NMR spectrum of (IIB) in CDCl$_3$ was as follows:

1.22 δ (d, J = 6.5 Hz, 3H, CH$_3$),
2.05–2.70 δ (m, 2H, C(2)H$_2$),
4.46 δ (dq, J = 6.5 Hz and J < 1Hz, 1H, C(5)H),
4.60–5.10 δ (m, 1H, C(3)H),
5.37 δ (c, W$_H$ = 6.0 Hz, 1H, C(4)H),
6.29 δ (m, W$_H$ = 6.5 Hz, 1H, C(1)H), and
6.37 δ (broad s, 1H, NH).

EXAMPLE 3

Preparation of adriamycin (IV) and its β-anomer (V)

A solution of 40 mg. of (IC) in 3 ml. of methylene dichloride was treated with 80 mg. of mercuric oxide, 20 mg. of mercuric bromide and molecular sieve (3 A, Merck). The mixture was stirred for one hour at room temperature, after which there were added thereto, 40 mg. of (IIB), prepared as in Example 2. After two hours stirring, an additional 40 mg. of (IIB) were added, and stirring was continued for 6 hours more. Then, 20 ml. of chloroform were added, and the suspension was filtered. The clear solution was evaporated under reduced pressure to yield a residue which was dissolved in 15 ml. of 0.1N sodium hydroxide. After standing for 30 minutes at room temperature, the pH of the aqueous solution was adjusted to 8.4 with 0.1N aqueous hydrogen chloride. The aqueous solution was repeatedly extracted with chloroform, and the combined chloroform extracts were dried over anhydrous sodium sulphate, filtered and evaporated to a residue. The residue was taken up in solution with 20 ml. of 0.1N aqueous hydrogen chloride and left standing at room temperature for 24 hours. An equal volume of chloroform was added and, under stirring, the pH was raised to 8.4 with 0.1N aqueous sodium hydroxide. The final product, which was a mixture of adriamycin (IV) (α-anomer) and a second component which is the α-anomer of adriamycin (V) was recovered in the chloroform phase in a total yield of 80%. Adriamycin (β-anomer) (V) is also called 1'-(S)-adriamycin according to the nomenclature of Cahn et al, Experientia, 1956, 12, 81. Evaporation of the chloroform solution to 0.5 ml., and the addition of a drop of dilute methanolic hydrogen chloride causes the main product (adriamycin, α-anomer) (IV) to precipitate as the hydrochloride in crystalline form. The adriamycin hydrochloride (β anomer) has [α]$_D^{20}$ + 463° (c = 0.07 MeOH) TLC on silica gel plat buffered at pH 7 (M/15 phosphate), solvent system CHCl$_3$—MeOH—H$_2$O (130:60:10 by vol.), Rf = 0.35.

EXAMPLE 4

Preparation of 1-chloro-2,3,6-trideoxy-3-trifluoroacetamido-4-trifluoroacetoxy-α-L-arabinohexopyranose (IIIB)

One gram of 2,3,6-trideoxy-3-trifluoroacetamido-L-arabinohexopyranose, prepared in accordance with the description set forth on page 10 of our copending patent application G 324 entitled "Daunomycins, process for their preparation and uses thereof", was suspended in 20 ml of anhydrous diethyl ether and treated at 0° C. with trifluoroacetic anhydride. After allowing the suspension to stand for two hours at 0° C. and 1 hour at room temperature, the solvent was removed under reduced pressure and the residue crystallized from dichloromethane to yield 2,3,6-trideoxy-1-trifluoroacetoxy-3-trifluoroacetamido-4-trifluoroacetoxy-L-arabinohexopyranose (IIIA). The thus obtained (IIIA) was treated with anhydrous gaseous hydrogen chloride as described in Example 2 to give a quantitative yield of 1-chloro-2,3,6-trideoxy-3-trifluoro-acetamido-4-tri-fluoroacetoxy-α-L-arabinohexopyranose (IIIB). The NMR spectrum of (IIIB) in CDCl$_3$ was as follows:

1.30 δ (d, J = 6.0 Hz 3H, CH$_3$),
2.25–2.80 δ (m, 2H, C(2)H$_2$),
4.20 –4.65 δ (m, 1H, C(5)H),
4.65–5.15 δ (m, 2H, C(3)H and C(4)H),
6.25 δ (m, W$_H$ = 6.0 Hz, 1H, C(1)H), and
6.45 δ (broad s, 1H, NH).

EXAMPLE 5

Preparation of 4'-epiadriamycin (VI) and its β-anomer (VII)

A solution of 0.7 gm. of (IC), prepared as described in Example 1 in 35 ml. of methylene dichloride was treated with 1.4 gm. of mercuric oxide, 0.35 gm. of mercuric bromide and an excess of molecular sieve (3 A, Merck) as dehydrating agent.

The mixture was stirred at room temperature, and two 0.35 gm. portions of (IIIB) were added after 1 and 3 hours respectively. The stirring was continued overnight, after which 50 ml. of chloroform were added. The reaction mixture was filtered and the filtrate was evaporated under vacuum to yield a residue which was dissolved in MeOH, refluxed 15 minutes and evaporated to dryness. The residue was dissolved in 50 ml. of 0.1N sodium hydroxide and 10 ml. of acetone. After 30 minutes standing at room temperature, the pH was adjusted to 8.4 with dilute aqueous hydrogen chloride. The solution was then repeatedly extracted with chloroform. The combined chloroform extracts were dried with anhydrous sodium sulphate, filtered, and evaporated under vacuum. The resulting residue was taken up in 50 ml. of 0.1N aqueous hydrogen chloride and left at room temperature for 36 hours. The acidic solution was washed by extraction with chloroform to eliminate traces of the aglycone, and then brought to pH 8.6 with stirring and in the presence of 50 ml. of chloroform by slowly adding 0.1N aqueous sodium hydroxide. The organic phase was separated, dried with anhydrous sodium sulphate, and concentrated to 10 ml. Upon careful addition of methanolic hydrogen chloride, a red precipitate was obtained. The precipitate was collected, washed with diethylether and dried. The product, amounting to 220mg. was a 70:30 (weight) mixture of 4'-epiadriamycin hydrochloride (α-anomer) (VI) and 4'-epiadriamycin hydrochloride (β anomer) (VII). The two anomers as free bases were then separated by chromatography on a silicic acid column.

4'-Epiadriamycin hydrochloride (α-anomer), has m.p. 185° C (dec) [α]$_D^{20}$ + 274° (c = 0.01 MeOH), TLC on silica gel plat buffered at pH 7 (M/15 phosphate), solvent system CHCl$_3$—MeOH—H$_2$O (130:60:10 by vol.) Rf: 0.55.

4'-Epiadriamycin (β anomer) Rf: 0.43 (same conditions).

The following inhibition zones for the hydrochlorides of the below listed compounds were obtained on agar-B-subtilis plates using the paper disc technique (diameter given in mm.):

| μg | adriamycin (IV) | 4'-epi-adriamycin; 70:30 (mixture of α- and β-anomers) (VI and VII) | 4'-epi-adriamycin (α-anomer) (VI) | 4'-epi-adriamycin (β-anomer) (VII) |
|---|---|---|---|---|
| 5  | —  | 19 | 19 | 15 |
| 10 | 21 | 21 | 21 | 15.5 |
| 15 | —  | 22 | 22 | 16 |
| 20 | 23 | 23 | 23 | 17 |

BIOLOGICAL ACTIVITY

The antitumor activity of the novel compounds of the invention, i.e., 4'-epi-adriamycin, both as a 70:30 mixture of the α and β-anomers and as the α-anomer alone was evaluated on several transplanted tumors in mice, and in in vitro tests, in comparison with the known antitumor agent adriamycin. The results of these tests are given in the following tables.

Ascites Sarcoma 180

The tests were carried out on groups of 10 mice (Swiss CD 1). The compounds under examination were administered intraperitoneally in varying doses to the test animals one day after intraperitoneal inoculation with 1 × 10$^6$ tumor cells per animal. The average survival time is given in Table 1 as a percentage of the survival time of untreated animals, which is arbitrarily designated as 100%. Also given in Table 1 are the number of long term survivors.

TABLE 1

| | Action on Ascites Sarcoma 180 | | |
|---|---|---|---|
| Compound | Dose mg/Kg | Average Survival time (%) | Long Term Survivors (after 60 days) |
| Control | — | 100 | 0/30 |
| Adriamycin | 1 | 169 | 0/10 |
|  | 5 | 276 | 2/10 |
| 4'-Epi-adriamycin (70:30 mixture of α and β-anomers) | 0.2 | 124 | 0/10 |
|  | 1 | 247 | 7/30 |
|  | 1.5 | 342 | 12/20 |
|  | 2.25 | 345 | 9/20 |
|  | 5 | 172 | 0/10 |
| 4'-Epi-adriamycin (α-anomer) | 0.5 | 135 | 0/10 |
|  | 2 | 184 | 0/10 |
|  | 10 | 234 | 1/8 |

Transplanted Gross Leukemia

Inbred C$_3$H/He mice were intravenously inoculated with 2 × 5 10$^6$ leukemia cells/mouse and treated, intravenously, from the first to the fifth day after inoculation with the compounds under examination. The average survival time percentage and the number of long term survivors are given in Table 2.

TABLE 2

| | Action on Transplanted Gross Leukemia | | |
|---|---|---|---|
| | Dose | Average Survival time (%) | Long Term Survivors (after |
| Compound | mg/Kg | Exp. 1 | Exp. 2 | 60 days) |
| Control | — | | | 0/30 |
| Adriamycin | 2 | 183 | | 0/10 |
|  | 2.5 | 208 | 186 | 0/20 |
|  | 2.75 | 208 | | 0/10 |
|  | 3 | | 186 | 0/10 |
|  | 3.6 | | 200 | 0/10 |
| 4'-Epi-adriamycin (70:30 mixture of α and β-anomers) | 2 | 133 | | 0/10 |
|  | 2.5 | 142 | 143 | 0/20 |
|  | 2.75 | 142 | | 0/10 |
|  | 3 | | 157 | 0/10 |

TABLE 2-continued

| Compound | Dose mg/Kg | Average Survival time (%) Exp. 1 | Exp. 2 | Long Term Survivors (after 60 days) |
|---|---|---|---|---|
| | 3.6 | | 171 | 0/10 |

$L_{1210}$ Leukemia

Inbred $BDF_1$ mice were intraperitoneally inoculated with $10^5$ leukemia cells/mouse, and then treated (intraperitoneally) 5 times (every two hours) on days 1 and 2 after the tumor inoculation with varying doses of the compounds under examination. The average survival time percentage and the number of long term survivors are given in Table 3.

TABLE 3

| | | Action on $L_{1210}$ Leukemia | |
|---|---|---|---|
| Compound | Dose mg/Kg | Average Survival time (%) | Long Term Survivors (after 60 days) |
| Adriamycin | 0.75 | 160 | |
| | 1 | 155 | 1/10 |
| | 1.25 | 175 | |
| 4'-Epi-adriamycin (70:30 mixture of α and β-anomers) | 0.75 | 140 | |
| | 1 | 140 | |

Solid Sarcoma 180

Swiss CD 1 mice were subcutaneously grafted with fragments of neoplastic (Solid Sarcoma 180) tissue and treated intravenously according to different schedules as shown in Table 4. The growth of the tumors were evaluated by caliper measurement on the 10th day after the tumor implants. The results, including tumor growth inhibition, and the average survival time percentage are given in Table 4.

TABLE 4

| | | Activity on Solid Sarcoma 180 | | | |
|---|---|---|---|---|---|
| Compound | mg/Kg Dose mg/Kg | Schedule of Treatment | % Inhibition tumor growth | Average Survival time (%) | Toxic Deaths (at 10th day) |
| Adriamycin | 1.25 | Subcutaneously every 2 hrs. for 5 times at days 1 and 3. | 69 | 112 | 0/10 |
| | 1.75 | | 75 | 87 | 1/10 |
| | 2.45 | | | 32 | 6/10 |
| 4'-Epi-adriamycin (70:30 mixture of α- and β-anomers) | 1.25 | " | 31 | 105 | 0/10 |
| | 1.75 | | 47 | 100 | 0/10 |
| | 2.45 | | 61 | 97 | 0/10 |
| Adriamycin | 2.5 | Intravenously once a day on days 1,2,3,4,5. | 54 | | 0/10 |
| | 3.5 | | | | 7/10 |
| 4'-Epi-adriamycin (70:30 mixture of α- and β-anomers) | 2.5 | " | 31 | | 0/10 |
| | 3.5 | | 46 | | 0/10 |
| | 4.5 | | 43 | | 0/10 |
| Adriamycin | 2 | Intravenously twice a day on days 1,2,3. | 70 | 100 | 1/10 |
| | 2.5 | | 71 | 100 | 2/10 |
| | 3 | | | 57 | 6/10 |
| 4'-Epi-adriamycin (70:30 mixture of α- and β-anomers) | 3 | " | 45 | 133 | 0/9 |
| | 4 | | 57 | 106 | 0/10 |
| | 5 | | 59 | 84 | 1/10 |

Tests in vitro on the Formation of foci by Moloney Sarcoma Virus (MSV)

The test compounds were evaluated on mouse embryo fibroblast cultures infected with MSV and on similar uninfected cultures. After a treatment of 3 days, the inhibiting doses ($ID_{50}$) were evaluated on cell proliferation in uninfected cultures (cytotoxic action) and on MSV foci formation in infected cultures (antiviral action). The results obtained are given in Table 5.

TABLE 5

| Compound | Antiviral Action $ID_{50}$ γ/ml | Cytotoxic Action $ID_{50}$ γ/ml |
|---|---|---|
| Adriamycin | 0.005 | 0.01 |
| 4'-Epi-adriamycin | >0.006 | 0.01 |

Activity on MSV Production

MSV infected cultures were treated for 3 days, and the virus yields were determined in the cell and supernatant medium by focus assay in the presence of leukemia virus. The results are given in Table 6.

TABLE 6

| Compound | Dose (γ/ml) | FFU/ml |
|---|---|---|
| Control | | $4.7 \times 10^4$ |
| 4'-Epi-Adriamycin | 0.05 | $4 \times 10^2$ |
| | 0.0250 | |

Test in vitro on the Cloning Efficiency of Hela cells

After treatment for 2,8 or 24 hours, HeLa cells were seeded (200 cells per plate) and the number of colonies determined 8 days later.

The $ID_{50}$ represents the dose which gives a 50% of inhibition of colonies. The results obtained are given in Tables 7 and 8.

TABLE 7

| Compound | Dose μg/ml | Average Number of Colonies After Treatment Periods: | | |
|---|---|---|---|---|
| | | 2h | 8h | 24h |
| Control | — | 132 | 125 | 223 |
| Adriamycin | 1 | 21 | 8 | 0 |
| | 0.5 | 42 | 16 | 0 |
| | 0.25 | 46 | 38 | 20 |
| | 0.1 | 79 | 73 | 48 |
| | 0.05 | 100 | 96 | 76 |
| 4'-Epi-adriamycin (α-anomer) | 1 | 57 | 36 | 29 |
| | 0.5 | 101 | 92 | 52 |
| | 0.25 | 103 | 150 | 199 |
| | 0.1 | 158 | 216 | |
| | 104 | | | |
| | $DI_{50}$ 0.17 μg/ml | $DI_{50}$ 0.14 μg/ml | $DI_{50}$ 0.016 μg/ml | |
| | $DI_{50}$ 0.85 | $DI_{50}$ 0.7 | $DI_{50}$ 0.36 | |

TABLE 7-continued

| Compound | Dose μg/ml | Average Number of Colonies After Treatment Periods: | | |
|---|---|---|---|---|
| | | 2h μg/ml | 8h μg/ml | 24h μg/ml |

TABLE 8

| Compounds | Dose μg/ml | Average Number of Colonies After Treatment of Periods: | | |
|---|---|---|---|---|
| | | 2h | 8h | 24h |
| Control | — | 156 | 189 | 136 |
| Adriamycin | 0.5 | 27 | 14 | n.d. |
| | 0.25 | 92 | 28 | 43 |
| | 0.125 | 166 | 103 | 69 |
| | | $DI_{50}$ 0.35 μg/ml | $DI_{50}$ 0.18 μg/ml | $DI_{50}$ 0.125 μg/ml |
| 4'-Epi-adriamycin (α-anomer) | 1 | 105 | 27 | 17 |
| | 0.5 | 130 | 45 | 38 |
| | 0.25 | 109 | 43 | 46 |
| | 0.125 | 245 | 170 | 100 |
| | | $DI_{50}$ 5 μg/ml | $DI_{50}$ 0.2 μg/ml | $DI_{50}$ 0.2 μg/ml |

Tests in vitro on the Cardiotoxic Activity

The cardiotoxic activity of the test compounds were evaluated in vitro on myocardial cells of BALB/c or CD 1 newborn mice (Necco A., Dasdia T. IRCS, 2 : 1293, 1974) Adriamycin causes a 50% decrease of beating in 2 hours at a dose of 0.5 μg/ml.

4'-Epi-adriamycin (70:30 mixture of α and β anomers), at doses up to 5 μg/ml did not substantially alter the beating rate. This is shown in the drawing.

Variations can, of course, be made without departing from the spirit and scope of the invention.

Having thus described our invention, what we desire to secure by Letters Patent and hereby claim is:

1. A compound of the formula

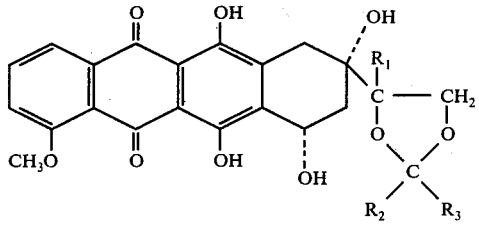

wherein each of $R_1$, $R_2$ and $R_3$ is independently selected from the group consisting of hydrogen and $C_1$–$C_4$ alkyl, or $R_2$ and $R_3$, together with the carbon atom to which they are bound may form a saturated or unsaturated ring of 3–8 carbon atoms.

2. A compound as claimed in claim 1, wherein $R_1$, $R_2$ and $R_3$ are methyl.

* * * * *

UNITED STATES PATENT OFFICE
CERTIFICATE OF CORRECTION

Patent No. 4,098,798    Dated July 4, 1978

Inventor(s) Federico Arcamone et al

It is certified that error appears in the above-identified patent and that said Letters Patent are hereby corrected as shown below:

Title page, line 1 of Abstract: "known antibiotics" should read -- known antitumor antibiotic --.

Column 1, line 16: "antibiotics" should read -- antibiotic --; line 19: "4'-epiardriamycin" should read -- 4'-epi-adriamycin --.

Column 3, Formula IIA, lines 51-60:

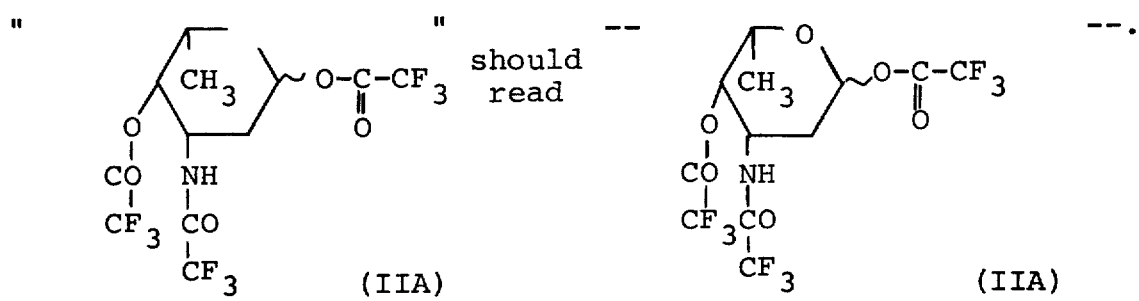

Column 4, lines 52-53: "consensed" should read -- condensed --; lines 54-55: "-arabinohexopyranosc" should read -- -arabino-hexopyranose --.

Column 5, line 47: "(IIA) and (IIA)" should read -- (IIA) and (IIIA) --.

Column 8, line 39: "$\alpha$-anomer" should read -- $\beta$-anomer --; lines 59-61: these lines should read as follows:
-- description set forth in copending application Serial No. 560,105, filed 3/19/75, now U.S. Patent No. 4,039,663, issued August 2, 1977, was suspended in 20 --.

UNITED STATES PATENT OFFICE
CERTIFICATE OF CORRECTION

Patent No. 4,098,798          Dated July 4, 1978

Inventor(s) Federico Arcamone et al

It is certified that error appears in the above-identified patent and that said Letters Patent are hereby corrected as shown below:

Column 9, line 31: "MeOH" should read -- methanol --.

Column 12, Table 7, line 2 from the bottom:
"0.1   104         158         216              "   should read
        $DI_{50}0.85$  $DI_{50}0.7$  $DI_{50}0.36$ -- 0.1      104         158         216          --.
       $DI_{50}0.85$  $DI_{50}0.7$  $DI_{50}0.36$ Column 13, line 26: "were" should read -- was --.

Signed and Sealed this

Twenty-fifth Day of September 1979

[SEAL]

Attest:

LUTRELLE F. PARKER

Attesting Officer          Acting Commissioner of Patents and Trademarks